United States Patent [19]

Jacobsen

[11] Plant 4,842

[45] Apr. 27, 1982

[54] POINSETTIA NAMED TOPWHITE

[75] Inventor: Peter Jacobsen, Skibby, Denmark

[73] Assignee: Paul Ecke, Jr., Encinitas, Calif.

[21] Appl. No.: 197,951

[22] Filed: Oct. 17, 1980

[51] Int. Cl.[3] ..... A01H 5/00

[52] U.S. Cl. ..... Plt./86

[58] Field of Search ..... Plt./86

[56] References Cited

U.S. PATENT DOCUMENTS

P.P. 3,082 3/1972 Hegg ..... Plt./86

*Primary Examiner*—James R. Feyrer

*Attorney, Agent, or Firm*—Chas. W. Rummler

[57] ABSTRACT

A new poinsettia cultivar distinguished by the unique characteristic of a whiter bract as compared with the former white variety of the Annette Hegg line shown and described in U.S. Plant Pat. No. 3,082. Otherwise this new plant has retained the important self branching, easy rooting, low temperature blooming and medium height characteristic of the Hegg family of poinsettias.

2 Drawing Figures

BACKGROUND OF THE NEW PLANT

My new poinsettia originated as a mutation of the well known red variety of the Annette Hegg family (U.S. Plant Pat. No. 2,962) induced by irradiation and was discovered by me in my greenhouse at Maaloy, Denmark, among other poinsettia plants which I had irradiated in the course of my research carried on with the object of producing new poinsettia varieties for the commercial market. I selected this particular mutation for propagation and test because of its distinctive white and cleaner color and my propagation of this new plant, by cuttings, through successive generations at Maaloy, Denmark, has shown that the novel and distinctive characteristics of the original plant hold true from generation to generation and appear to be firmly fixed. Commercial propagation of this new cultivar by means of vegetative cuttings is now being done at Encinitas, Calif.

DESCRIPTION OF THE DRAWINGS

My new variety of poinsettia is illustrated by the accompanying full color photographic drawings, the upper one of which shows a full face view of the flower cluster and surrounding bracts and the lower view shows a potted plant in full bloom, the color reproduction being as nearly true as is reasonably possible to obtain by conventional photographic procedures.

DESCRIPTION OF THE NEW PLANT

The following is a detailed description of my new variety of poinsettia plant as observed at Encinitas, Calif., with color designations according to the R.H.S. Colour Chart published by The Royal Horticultural Society of London, England.

THE PLANT

Origin: Mutation induced by irradiation.

Parentage: Annette Hegg Red (U.S. Plant Pat. No. 2,962).

Classification:

*Botanic.*—*Euphorbia pulcherrima.*

Form: Shrub.

Height: Short.

Growth habit:

*As a single stem.*—Upright and vigorous with self branching side shoots; may require a growth regulator.

*As a branched plant.*—Upright with very many stems producing a busy, full appearance.

Growth rate: Very fast. Rooting occurs in 15 to 20 days under automatic mist and the plant will bloom in about 8½ to 9 weeks at a night temperature of 16° to 18° C. during October and November. Under poor light conditions, a somewhat higher temperature may be required.

Foliage: Similar to the parent variety with respect to leaf size and aspect.

*Shape.*—Typical leaves are generally ovate-acuminate and seldom lobed.

*Color.*—Upper side — Between RHS 139A and 147A. Under side — Between RHS 137C and 147B.

*Retention.*—Long lasting, as in the case of the parent variety.

Bracts: With respect to size, shape and petiole, this cultivar has substantially the same characteristics as the parent variety.

*Color.*—Upper side — Near RHS 160C, with light green veining which varies from barely noticeable to moderate. Under side — Near RHS 160C but slightly greener. The bracts of this new cultivar are of a whiter and cleaner color than other varieties. If this variety is finished too cool, down to 14° to 15° C., the bract color may become pinkish. In the case of the former white variety of the Annette Hegg line, the color becomes a light yellow-green under the same conditions.

This new variety of poinsettia plant has substantially the same characteristics as the parent (U.S. Plant Pat. No. 2,962) in most appearance and cultural points except for the clean white color which is noticeably whiter than most other white poinsettias. The new plant has retained all of the important characteristics of the Hegg family of poinsettias, i.e., self branching, easy rooting, high cutting production, low temperature blooming, medium height, excellent leaf retention and relative freedom from disease. Also, this cultivar sets bud under warmer night greenhouse conditions than most other poinsettia varieties.

I claim:

1. A new and distinct poinsetta cultivar, substantially as herein shown and described, characterized particularly by the whiter and cleaner color of its bracts and its retention of the advantageous physical and growing characteristics of its red parent variety.

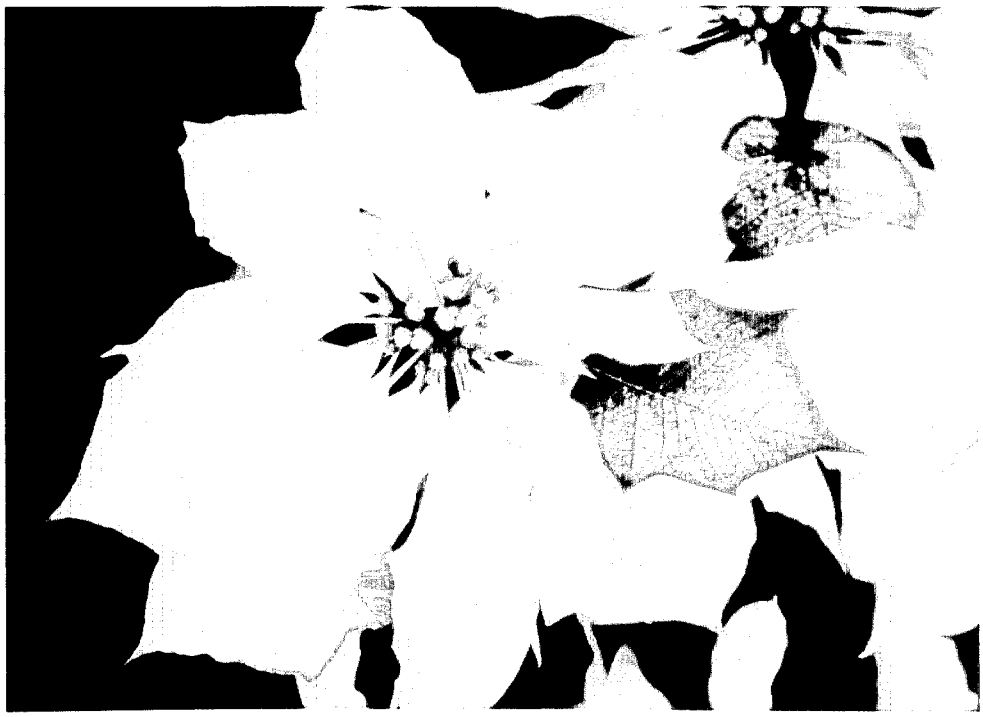
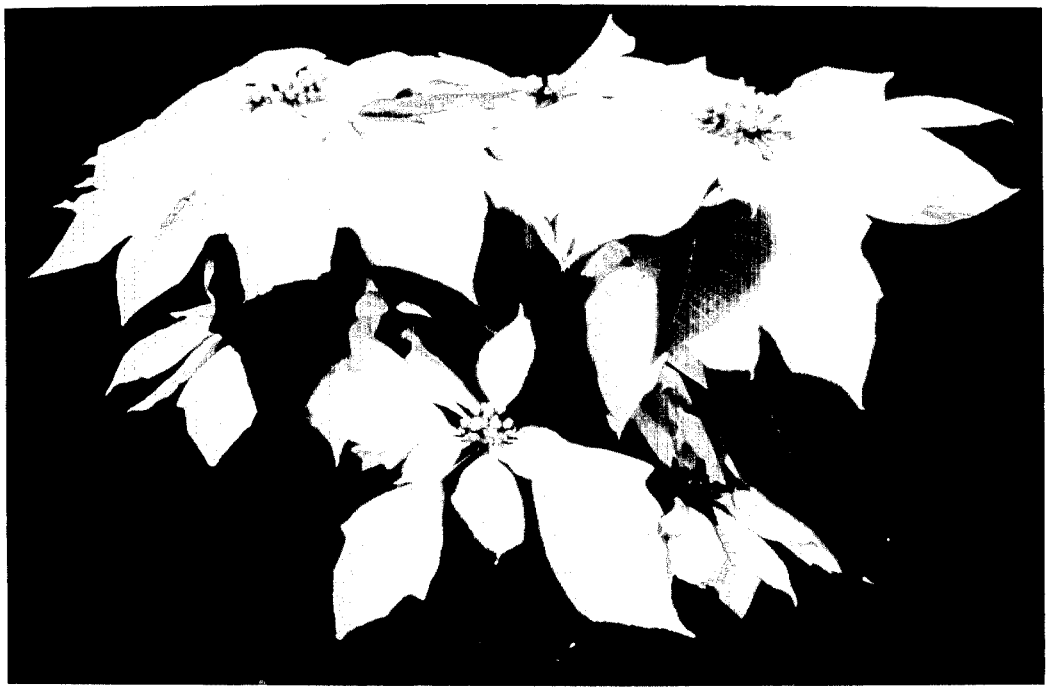

* * * * *